Figure 1:
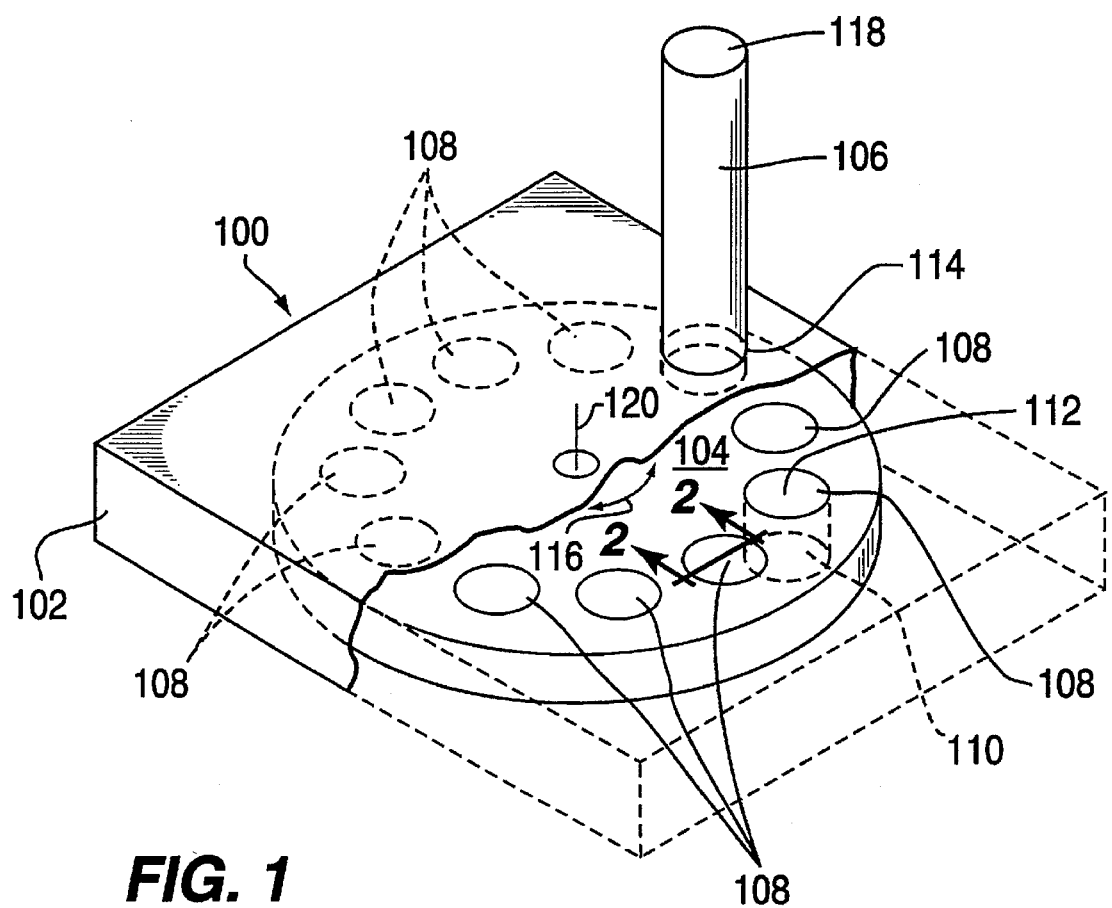
Figure 2:
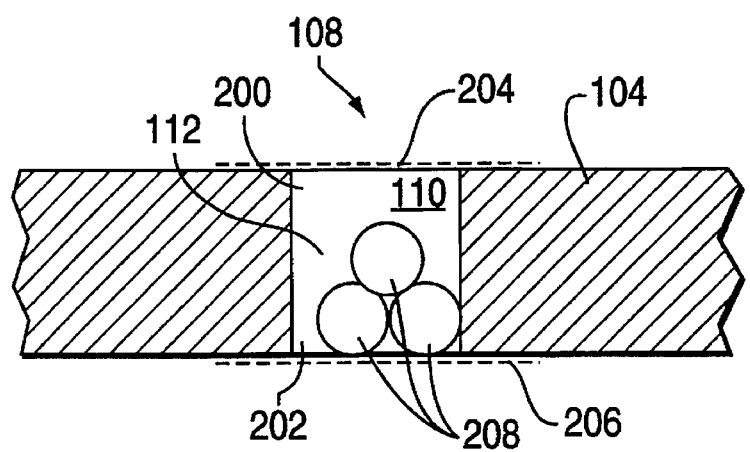

US005642727A

United States Patent [19]
Datta et al.

[11] Patent Number: 5,642,727
[45] Date of Patent: Jul. 1, 1997

[54] INHALER APPARATUS USING A TRIBO-ELECTRIC CHARGING TECHNIQUE

[75] Inventors: Pabitra Datta; Nitin V. Desai, both of Mercer, N.J.

[73] Assignee: David Sarnoff Research Center, Inc., Princeton, N.J.

[21] Appl. No.: 506,703

[22] Filed: Jul. 25, 1995

[51] Int. Cl.$^6$ .......................... A61M 15/00; A61M 16/10

[52] U.S. Cl. ................................ 128/203.15; 128/203.12; 128/202.25

[58] Field of Search ......................... 128/203.15, 203.21, 128/202.25, 203.12; 604/58; 239/102.1, 102.2

[56] References Cited

U.S. PATENT DOCUMENTS

| | | | |
|---|---|---|---|
| 2,470,296 | 5/1949 | Fields | 128/203.15 |
| 2,513,145 | 11/1950 | Chapple | 128/203.15 |
| 2,534,636 | 12/1950 | Stirn | 128/203.15 |
| 3,831,606 | 8/1974 | Damani | 128/266 |
| 3,971,377 | 7/1976 | Demani | 128/266 |
| 4,047,525 | 9/1977 | Kulessa et al. | 128/208 |
| 4,197,289 | 4/1980 | Sturzenegger et al. | 424/21 |
| 4,570,630 | 2/1986 | Elliott et al. | 128/203.15 |
| 4,627,432 | 12/1986 | Newell et al. | 128/203.15 |
| 4,664,107 | 5/1987 | Wass | 128/200.23 |
| 4,811,731 | 3/1989 | Newell et al. | 128/203.15 |
| 4,889,114 | 12/1989 | Kladders | 128/203.15 |
| 5,031,610 | 7/1991 | Armstrong et al. | 128/200.23 |
| 5,115,803 | 5/1992 | Sioutas | 128/200.23 |
| 5,161,524 | 11/1992 | Evans | 128/203.15 |
| 5,176,132 | 1/1993 | Drought et al. | 128/203.15 |
| 5,186,164 | 2/1993 | Rughuprasad | 128/200.14 |
| 5,239,993 | 8/1993 | Evans | 128/203.15 |
| 5,243,970 | 9/1993 | Ambrosio et al. | 128/203.15 |
| 5,263,475 | 11/1993 | Altermatt et al. | 123/203.15 |
| 5,301,666 | 4/1994 | Lerk et al. | 128/203.15 |
| 5,327,883 | 7/1994 | Williams et al. | 128/203.12 |
| 5,469,843 | 11/1995 | Hodson | 604/58 |
| 5,476,093 | 12/1995 | Janiken | 128/203.15 |

FOREIGN PATENT DOCUMENTS

| | | | |
|---|---|---|---|
| 2264237 | 8/1993 | United Kingdom | 128/203.12 |
| 9013328 | 11/1990 | WIPO | 128/203.15 |
| 9119254 | 12/1991 | WIPO | 128/203.15 |
| WO93/0983 | 5/1993 | WIPO | A61M 15/00 |
| WO94/08552 | 4/1994 | WIPO . | |
| WO94/13271 | 6/1994 | WIPO | A61K 9/72 |
| WO94/23772 | 10/1994 | WIPO . | |
| WO95/00127 | 1/1995 | WIPO | A61K 9/72 |

*Primary Examiner*—Vincent Millin
*Assistant Examiner*—V. Srivastava
*Attorney, Agent, or Firm*—William J. Burke

[57] ABSTRACT

A tribo-inhaler having a container portion for electrostatically retaining a predefined dose of medicament powder, where the medicament is tribo-electrically charged; and apparatus, attached to the container portion, for extracting said medicament powder from the container portion. The container portion contains a plurality of polymeric beads that have diameters of approximately 50 to 200 microns. Each of the polymeric beads has a specific quantity of dry powder medicament electrostatically adhered to its surface. To remove the medicament from the cavity, a patient merely inhales air through the container portion. The air flow forcefully moves the beads within the container portion causing the medicament to dislodge from the beads and be carried by the air flow into the lungs of the patient.

18 Claims, 3 Drawing Sheets

INHALER APPARATUS USING A TRIBO-ELECTRIC CHARGING TECHNIQUE

The invention relates to medication inhalers and, more particularly, to apparatus for electrostatically retaining a medicament powder within an inhaler using a tribo-electric charging technique.

BACKGROUND OF THE DISCLOSURE

Inhalers are used to administer pre-determined quantities (doses) of inhalable dry powder medicament to the lungs of a patient. Generally, inhalers are mechanical systems that generate a metered cloud of medicament that is inhaled by a patient. Many of these prior art inhaler devices use chloroflourocarbon (CFC) gas to facilitate generation of the metered cloud of medicament. However, since CFCs are no longer used in consumer products, other techniques for generating the medicament cloud have been explored.

One example of a non-CFC, prior art inhaler is disclosed in U.S. Pat. No. 4,811,731 issued Mar. 14, 1989 (the "'731 patent"). This patent discloses an inhaler that contains a plurality of measured doses of medicament stored in a blisterpack. Upon use, one of the blisters in the blisterpack is punctured and a patient inhales the medicament from the punctured blister via a mouthpiece of the inhaler. In the '731 patent, the medicament dosage varies with the amount of force with which the patient inhales. Since inhalation of a powder from a blisterpack is rather difficult and a patient does not repeatedly inhale with the same force each time the medication is taken, the medicament dosage that is actually consumed can vary greatly from dose to dose.

Therefore, a need exists in the art for an inhaler that, over a wide range of inspirable flow rates, maximizes drug propagation to the lungs and provides, with each use of the inhaler, substantially identical doses of medicament to the lungs.

SUMMARY OF THE INVENTION

The present invention overcomes the disadvantages associated with prior art inhalers by using a tribo-electric charging technique to retain a medicament powder within an inhaler apparatus. This unique inhaler apparatus has been dubbed a tribo-inhaler. The tribo-inhaler comprises a container portion within which is electrostatically retained a predefined dose of medicament powder, where the powder is tribo-electrically charged, and a mouthpiece or inhalation tube, attached to the container portion, for extracting the medicament powder from the container portion.

BRIEF DESCRIPTION OF THE DRAWINGS

The teachings of the present invention can be readily understood by considering the following detailed description in conjunction with the accompanying drawings, in which:

FIG. 1 depicts partial section, perspective view of a first embodiment of the tribo-inhaler;

FIG. 2 depicts cross-sectional view of a cavity within tribo-inhaler of FIG. 1;

FIG. 3 depicts a cross-sectional view of a tribo-electric charging apparatus for coating polymeric beads with powdered medicament; and FIG. 4 depicts a exploded view of a second embodiment of the tribo-inhaler; and FIG. 5 depicts a cross-sectional view of the second embodiment of the tribo-inhaler taken along line 5—5 of FIG. 4.

To facilitate understanding, identical reference numerals have been used, where possible, to designate identical elements that are common to the figures.

DETAILED DESCRIPTION

The present invention is an inhaler apparatus containing one or more predefined doses of medicament powder. The invention retains each dose within a container portion by an electrostatic charge generated using a tribo-electric charging technique.

Specifically, FIG. 1 depicts a partial sectional view of a first embodiment of the tribo-inhaler 100. The tribo-inhaler contains a housing 102 having a container portion 104 for retaining a medicament powder, and a flexible inhalation tube 106, attached to the housing, for extracting the medicament from the container portion. The container portion defines at least one cavity 108. Each cavity is an aperture 110 that passes through the container portion. The illustrative container portion 110 contains a plurality of cylindrical apertures that are evenly distributed in a circular pattern near the circumferential edge of the container portion. Medicament powder 112 is electrostatically retained within each cavity. The container portion is moveable relative to the housing, e.g., in response to user manipulation, the container portion rotates about a central axis 120 thereof (indicated by arrow 116). More specifically, the container portion is disk-shaped and is rotatable within the housing such that any one of the cavities can be positioned proximate one end (an inlet end 114) of the inhalation tube. The inhalation tube has its inner surface coated with a material, such as Teflon, that reduces adhesion of the medicament to the tube as the medicament passes through the tube. Additionally, the inhalation tube is generally flexible such that it easily folds along the top of the housing. As such, the inhaler easily fits within a shirt pocket or purse.

In use, a patient inhales through the outlet end 118 of the inhalation tube 106 to withdraw medicament from a selected cavity. To inhale subsequent doses, the container portion is rotated to position a different, unused cavity proximate the inlet end of the tube. Alternatively, a metered quantity and flow rate of compressed air could be applied to the cavity to transport the medicament to the patient's lungs.

More specifically, FIG. 2 depicts a cross-sectional view of a single cavity 108 of the tribo-inhaler 100 taken along line 2—2 of FIG. 1. The cavity is essentially a cylindrical aperture 110 through the container portion 104. The first and second ends 200 and 202 of the aperture are respectively enclosed by a first and second screen 204 and 206. Each screen is approximately 200 mesh. Alternatively, the screens could be perforated solid layers of plastic or metal having openings with diameters of approximately 5 to 10 microns.

The cavity contains at least one, and more typically, a plurality of beads 208. The surface of each bead is coated with a medicament powder 112. The powder adheres to the bead surface by electrostatic attraction generated by a tribo-electric charging technique. The process and apparatus used to tribo-electrically charge the beads and powder is discussed below with respect to FIG. 3.

The container portion is fabricated by forming, typically by drilling, evenly spaced apertures in a disk-shaped substrate. Typically, the substrate is manufactured of plastic. Alternatively, the container portion is manufactured of injection molded plastic and the cavities are formed by the mold. Screen 206 (lower screen) is affixed to the surface of the container portion to close second aperture end 202. A select number of medicament coated beads are placed into the cavity, then the first screen 204 (upper screen) is affixed to the container portion surface to close first aperture end 200. The screens are typically affixed by an adhesive such as epoxy.

When a cavity is positioned proximate the inlet end of the inhalation tube and air is inhaled therethrough, air passes through the second screen, the cavity, and the first screen. As the air passes through the cavity, the beads are carried upwards until they impact the first screen. Since the beads impact the screen with substantial force, the medicament coating is dislodged from the surface of the beads. The dislodged medicament enters the inlet end of the inhalation tube as a cloud of medication and the tube carries the medicament to the patient that had inhaled on the outlet end of the inhalation tube. In this manner, a metered dose of medication is delivered to the patient's lungs.

Figure 3:
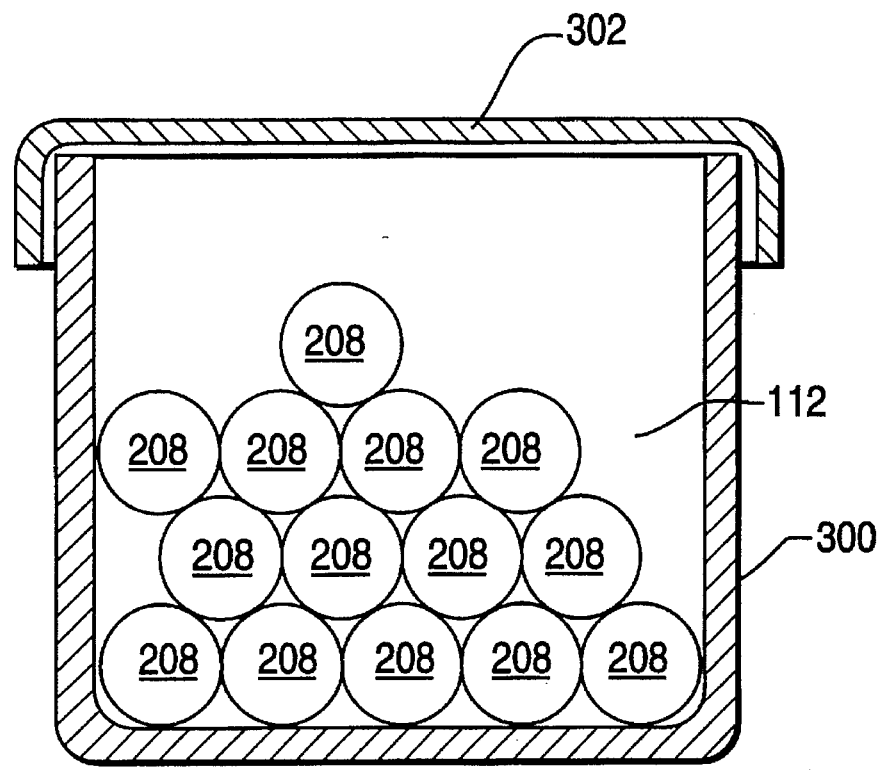

FIG. 3 depicts apparatus for tribo-electrically charging a medicament powder 112 so that the powder adheres to a plurality of beads 208. Specifically, the apparatus contains an enclosed bead container 300 having a lid 302, a plurality of beads 208, and a medicament powder 112. The beads and powder are mixed by shaking the container for one to ten minutes. During this period, the powder becomes tribo-electrically charged and the powder 112 electrostatically adheres to the beads 208.

More specifically, the beads have a diameter of between 50 and 200 microns and are fabricated of one of the following materials Teflon, polyvinylidene fluoride, polypropylene, dyed polypropylene, flouro-treated glass, glass, amino-treated glass, polystyrene, titanium dioxide-filled polyethylene and the like. In use, the medicament and beads are added to the container 300, the lid of the container is closed and the beads and medicament mixture is shaken for one to ten minutes. During the shaking process, a charge accumulates on the particles of the powder. Once charged, the medicament particles uniformly coat the surface of each bead.

The amount and polarity of the charge on the medicament particles depends upon the fabrication material of the beads. By measuring the charge-to-mass ratio of the powder using a faraday cage, the inventors have found that by selecting a particular bead material the charge characteristics are controllable. For example, charging a mometasone furoate (MF) powder in a glass container using four beads having 100 micron diameters at 70 degrees Fahrenheit and 45% relative humidity, resulted in the charge-to-mass ratios for various bead materials shown in TABLE 1.

TABLE 1

Charge-to-mass ratios for various bead materials

| Bead Material | Charge Polarity | Ratio (µC/gm) |
| --- | --- | --- |
| Teflon | positive | 35 |
| Polyvinylidene fluoride | positive | 30 |
| Polypropylene | positive | 6.5 |
| Dyed polypropylene | positive | 10 |
| Flouro-treated glass | positive | 17.8 |
| Glass | negative | 6.5 |
| Amino-treated glass | negative | 39.8 |
| Polystyrene | negative | 42.7 |
| Titanium dioxide-filled polyethylene | negative | 7.7 |

By appropriate selection of the bead material, the charge-to-mass ratio can be varied from 6.5 to 43 mC/gm and the charge is either positive or negative. When retaining a medicament, a low microgram quantity of medicament (e.g., 2–10 mg) requires a relatively high charge-to-mass ratio and a high microgram quantity of medicament (e.g., 20–40 mg) requires a relatively low charge-to-mass ratio. Thus, flexible charging characteristics are useful in facilitating retention of a wide range of medicament dosages.

Once the beads are coated with medicament, the coated beads are placed into a cavity of the container portion. A specific dose of medicament is defined by selecting a particular number of coated beads for placement in the cavity. When the medicament is dislodged and inhaled, a metered dose of medication is inhaled by the patient.

Figure 5:
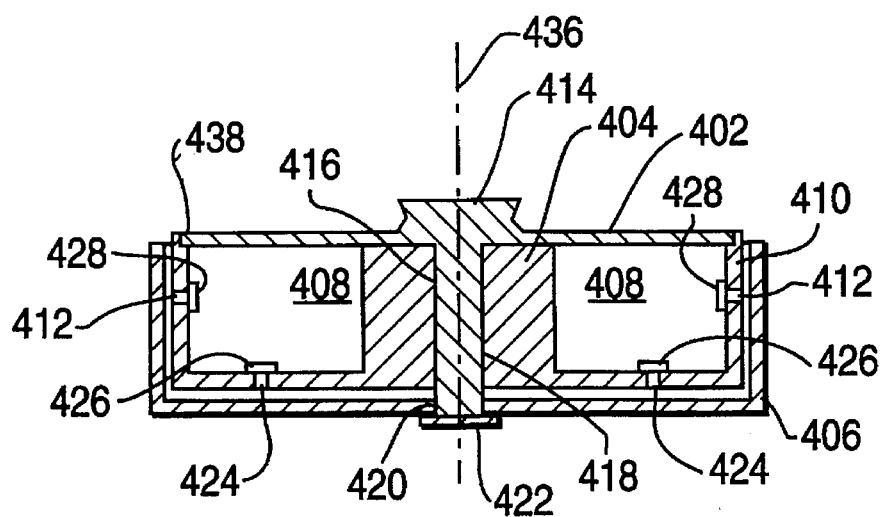
Figure 4:
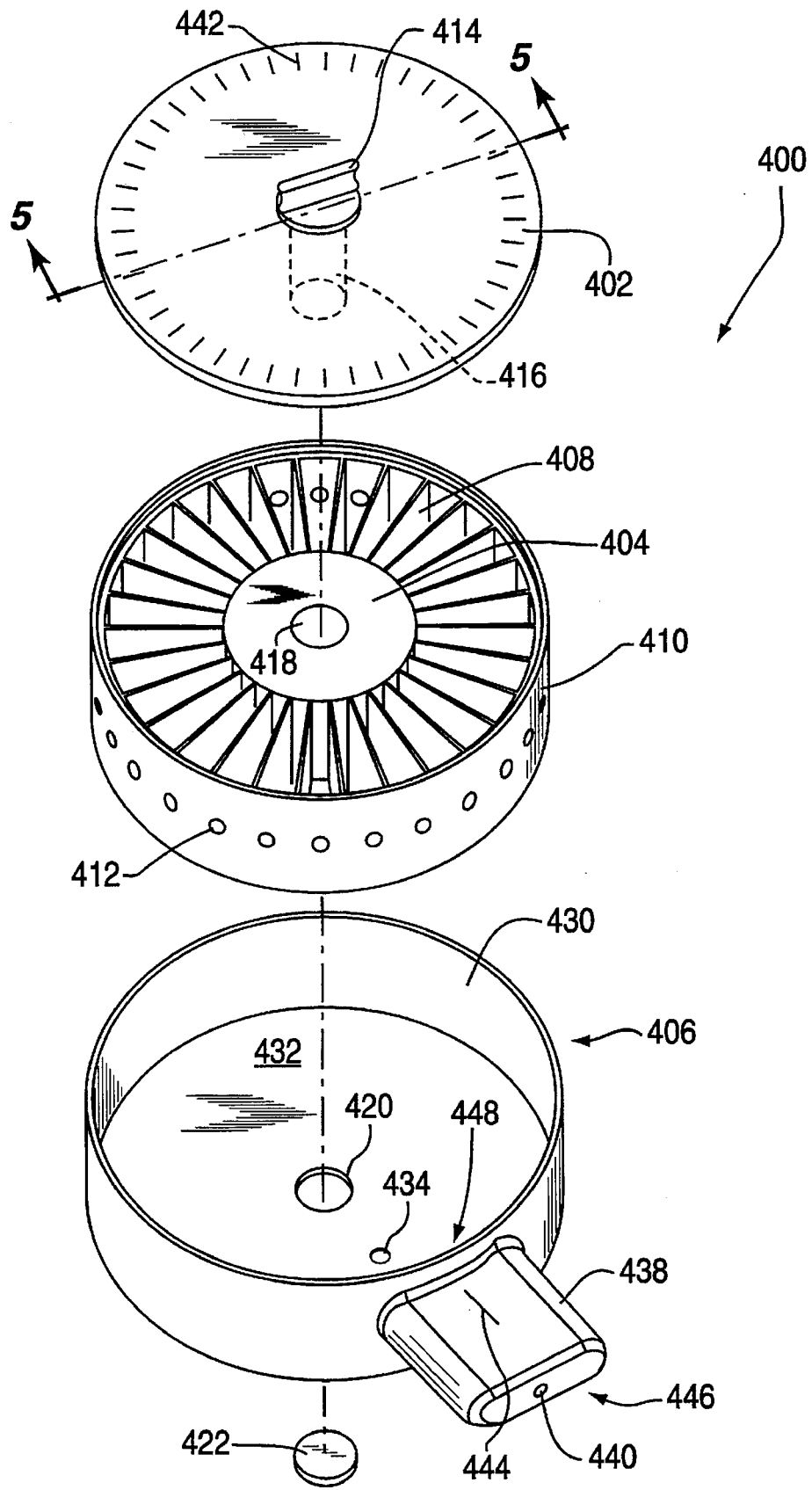

FIG. 4 depicts an exploded, perspective view of a second embodiment of the inventive tribo-inhaler 400. FIG. 5 is a cross-sectional view of the inhaler 400 taken along line 5—5 of FIG. 4. To best understand this embodiment of the invention, the reader should consult both FIGS. 4 and 5 while reading the following disclosure.

The inhaler 400 is an assembly having three main components; namely, a cover portion 402, a medicament container portion 404, and a outer housing 406. Each of the components is typically fabricated of injection molded plastic. The cover portion contains, affixed centrally to its top surface, a knob 414 and, affixed centrally to its bottom surface, a shaft 416. The shaft extends through a central bore 418 of the container portion 404 and is press fit therein. Additionally, the shaft rotatably extends through a central bore 420 in the outer housing 406. An end cap 422 is affixed, by gluing, welding, and the like, to the end of the shaft 416 such that the shaft can not be removed from the bore 420 but freely rotates therein. The cover portion and container portion rotate with respect to the outer housing about a central, longitudinal axis 436 of the shaft.

The medicament container 404 is substantially cylindrical and contains one or more cavities 408. Each cavity is substantially triangular in plan form having three walls and a bottom, where the top of the cavity is open to allow for the tribo-electrically charged beads (not shown) carrying the tribo-electrically charged medicament to be placed in the cavity. The bottom of the cavity contains an air inlet hole 424 that is covered with a mesh screen 426 having a mesh size that permits air to pass into the cavity but retains the beads within the cavity 408 (e.g., a mesh size of approximately 200 mesh). An outer circumferential wall 410 that forms one wall of each cavity defines a medicament extraction hole 412 into each cavity. These holes are covered by a mesh screen 428 located inside each cavity. Mesh screen 428 has a mesh size that retains the beads in the cavity, but permits the medicament to be extracted from the cavity (e.g., a mesh size of approximately 200 mesh).

The shaft 416 is press fit into bore 418 such that when knob 414 is rotated, the medicament container portion 404 rotates with respect to the outer housing 406. The outer circumferential edge of the cover portion interfits a lip 438 located on the upper edge of the wall 410. The interfit of the cover portion and the container portion seals each cavity such that air may only ingress and egress the cavity through the screens. To facilitate a sufficient seal, an adhesive may be applied about the lip to affix the edge of the cover portion to the lip.

The outer housing contains a cylindrical outer wall 430 supported by a bottom portion 432. The bottom portion defines an air intake hole 434 that is positioned at a radial distance from the longitudinal axis 436 of the shaft that is equivalent to the radial distance of the air inlet hole 424 from the longitudinal axis of the shaft. As such, the air intake hole 434 can be aligned with a selected air inlet hole 424 by rotating the knob 414.

Additionally, the outer housing 406 contains an inhalation tube in the form of a mouthpiece 438 that extends from the outer wall 430. The mouthpiece bore has an inlet end 448 and an outlet end 446. The mouthpiece contains a bore 440 that extends longitudinally through the mouthpiece and through the wall 430. The mouthpiece bore 440 is aligned with the medicament extraction hole 412 located in the container portion 404. As such, by manipulating the knob, a particular cavity can be rotated into alignment with the mouthpiece. Alignment being defined as a cavity position that aligns the air inlet hole 434 with an air intake hole 424 and aligns a medicament extraction hole 412 with the mouthpiece bore 440. Once alignment has been attained for a selected cavity, a user (patient) inhales on the mouthpiece, drawing air through the air inlet and air intake holes and through the cavity. As the air passes through the cavity, the beads are moved toward extraction hole 412 and impact the screen 428. The impact dislodges the medicament from the beads, where the medicament is carried by the air flow through the mouthpiece bore and into the user's lungs. To facilitate alignment and use of particular cavities, the cover portion is typically labeled with cavity numbers (not shown) and each cavity has an associated alignment mark 442. To achieve alignment, a selected cavity's alignment mark 442 is aligned with a reference mark 444 on the mouthpiece or some other indicia of alignment. Alternatively, alignment can be achieved using a mechanical lock mechanism that engages a detent when alignment with a particular cavity is achieved.

Although various embodiments which incorporate the teachings of the present invention have been shown and described in detail herein, those skilled in the art can readily devise many other varied embodiments that still incorporate these teachings.

What is claimed is:

1. An inhaler apparatus comprising:
   a container portion for electrostatically retaining a predefined dose of medicament powder, where said medicament is tribo-electrically charged, and wherein the container portion defines at least one cavity containing one or more beads to which the predefined dose of medicament powder is electrostatically adhered and
   an extracting means, attached to said container portion, for extracting said medicament powder from said container portion and from adherence to said beads.

2. The apparatus of claim 1 further comprising a first screen and a second screen for enclosing one or more beads in said cavity and allowing gas to pass through said cavity.

3. The apparatus of claim 2 wherein said extracting means further comprises an inlet end and an outlet end, where said inlet end is positioned proximate said first screen and, inhaling through said extracting means, said predefined dose of medicament is dislodged from said one or more beads and propagates from said inlet end to said outlet end.

4. The apparatus of claim 3 wherein said container portion defines a plurality of cavities.

5. The apparatus of claim 4 further comprising an housing for supporting said container portion and said extracting means, where said container portion is moveable relative to said housing and said extraction means to position any one of the plurality of cavities proximate to said inlet end of said extraction means.

6. The apparatus of claim 5 wherein said container portion is rotatable relative to said housing and said extraction means.

7. The apparatus of claim 2 wherein said cavity contains a plurality of beads.

8. The apparatus of claim 2 wherein at least one bead is a made of a polymeric material.

9. The apparatus of claim 2 wherein at least one bead is fabricated of a material that is selected to provide a specific charge-to-mass ratio for the medicament powder.

10. The apparatus of claim 2 wherein at least one bead has a diameter between 50 and 200 microns.

11. Inhaler apparatus comprising:
    a container portion defining a cavity;
    said cavity containing one or more beads having, deposited upon a surface of the beads, a coating of medicament powder, where said powder electrostatically adheres to said surface;
    a first screen and a second screen for enclosing one or more beads in said cavity and allowing a gas to pass through the cavity; and
    extracting means for extracting said medicament powder from said cavity and from said surface, said extracting means having an inlet end and an outlet end, where said inlet end is positioned proximate said first screen and, inhaling through said extracting means, said medicament powder is dislodged from said bead and propagates from said inlet end to said outlet end.

12. The apparatus of claim 11 wherein said container portion defines a plurality of cavities.

13. The apparatus of claim 12 further comprising a housing for supporting said container portion and said extracting means, where said container portion is moveable relative to said housing and said extracting means to position any one of the plurality of cavities proximate said inlet end of said extracting means.

14. The apparatus of claim 13 wherein said container portion is rotatable relative to said housing and said extracting means.

15. The apparatus of claim 11 wherein said cavity contains a plurality of beads.

16. The apparatus of claim 11 wherein at least one bead is a made of a polymeric material.

17. The apparatus of claim 11 wherein at least one bead is fabricated of a material that is selected to provide a specific charge-to-mass ratio for the medicament powder.

18. The apparatus of claim 11 wherein at least one bead has a diameter between 50 and 200 microns.

* * * * *